United States Patent
Chen et al.

(10) Patent No.: US 12,262,865 B2
(45) Date of Patent: Apr. 1, 2025

(54) METHOD OF IMAGE ENHANCEMENT FOR DISTRACTION DEDUCTION

(71) Applicant: BOSTON SCIENTIFIC SCIMED, INC., Maple Grove, MN (US)

(72) Inventors: Longquan Chen, Andover, MA (US); Jeffrey A. Meganck, N Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 506 days.

(21) Appl. No.: 17/685,280

(22) Filed: Mar. 2, 2022

(65) Prior Publication Data

US 2022/0280026 A1 Sep. 8, 2022

Related U.S. Application Data

(60) Provisional application No. 63/155,976, filed on Mar. 3, 2021.

(51) Int. Cl.
*A61B 1/00* (2006.01)
*G06T 7/00* (2017.01)
*G06T 7/20* (2017.01)

(52) U.S. Cl.
CPC ...... *A61B 1/000095* (2022.02); *G06T 7/0012* (2013.01); *G06T 7/20* (2013.01);
(Continued)

(58) Field of Classification Search
CPC . G06T 2207/10068; G06T 2207/20221; G06T 5/50; G06T 2207/20016; G06T 5/20; G06T 7/11; G06T 7/33; G06T 2207/10016; G06T 2207/10144; G06T 2207/20182; G06T 2207/20192; G06T 2207/20224;
(Continued)

(56) References Cited

U.S. PATENT DOCUMENTS 6,469,710 B1 10/2002 Shum et al.
8,803,962 B2 8/2014 Modell et al.
(Continued)

FOREIGN PATENT DOCUMENTS

JP 2019512178 A 5/2019

OTHER PUBLICATIONS

Mertens et al; "Exposure Fusion," 15th Pacific Conference on Computer Graphics and Applications, 9 pages, 2007.
(Continued)

*Primary Examiner* — Ajibola A Akinyemi
(74) *Attorney, Agent, or Firm* — Seager, Tufte & Wickhem, LLP

(57) ABSTRACT

Systems and methods related to combing multiple images are disclosed. An example method of combining multiple images obtained by an endoscope includes obtaining a first input image formed from a first plurality of pixels, wherein a first pixel of the plurality of pixels includes a first characteristic having a first value. The method also includes obtaining a second input image formed from a second plurality of pixels, wherein a second pixel of the second plurality of pixels includes a second characteristic having a second value. The method also includes subtracting the first value from the second value to generate a motion metric and generating a weighted metric map of the second input image using the motion metric.

16 Claims, 6 Drawing Sheets

(52) U.S. Cl.
CPC ............... *G06T 2207/10068* (2013.01); *G06T 2207/10144* (2013.01); *G06T 2207/20221* (2013.01)

(58) Field of Classification Search
CPC . G06T 2207/30004; G06T 2207/30056; G06T 2207/30084; G06T 5/70; G06T 7/0012; G06T 7/20; A61B 1/00009
USPC .......................................................... 382/128
See application file for complete search history.

(56) References Cited

U.S. PATENT DOCUMENTS

| | | | |
|---|---|---|---|
| 8,885,976 | B1 | 11/2014 | Kuo et al. |
| 9,053,558 | B2 | 6/2015 | Shen |
| 10,186,023 | B2 | 1/2019 | Pudipeddi et al. |
| 2002/0051058 | A1* | 5/2002 | Ito ........................... G06T 7/254 348/155 |
| 2011/0292257 | A1 | 12/2011 | Hatakeyama |
| 2012/0314103 | A1 | 12/2012 | Majewicz et al. |
| 2013/0028509 | A1 | 1/2013 | Moon et al. |
| 2013/0070965 | A1 | 3/2013 | Jang et al. |
| 2013/0321583 | A1* | 12/2013 | Hager ..................... G06T 7/579 348/46 |
| 2016/0267695 | A1 | 9/2016 | Opdenbosch |
| 2016/0301873 | A1 | 10/2016 | Molgaard et al. |
| 2017/0004636 | A1* | 1/2017 | Nett ...................... A61B 6/5205 |
| 2020/0211161 | A1 | 7/2020 | Trejo et al. |
| 2020/0265567 | A1 | 8/2020 | Hu et al. |
| 2021/0354096 | A1* | 11/2021 | Unnikrishnan ..... B01F 35/2202 |

OTHER PUBLICATIONS

IDAR, "Image Processing Laplace Blending," UNIK4690, Spring 2016 Lectures, 14 pages, Jan. 29, 2016, [Accessed on May 26, 2022].

Mertens et al, "Exposure Fusion: A Simple and Practical Alternative to High Dynamic Range Photography," Computer Graphics Forum, vol. 28, No. 1, pp. 161-171, Mar. 1, 2009.

International Search Report and Written Opinion for International Application No. PCT/US2022/018565 dated Jun. 24, 2022.

"Power Function" Encyclopedia of Mathematics, 3 pages, Feb. 7, 2011, Accessed May 31, 2022.

* cited by examiner

METHOD OF IMAGE ENHANCEMENT FOR DISTRACTION DEDUCTION

CROSS REFERENCE TO RELATED APPLICATIONS

This application claims the benefit of and priority to U.S. Provisional Patent Application Ser. No. 63/155,976 filed on Mar. 3, 2021, the disclosure of which is incorporated herein by reference.

TECHNICAL FIELD

The present disclosure relates to image processing techniques and more particularly, to fusing multiple images captured during a medical procedure, whereby fusing the multiple images includes merging selected portions of various weighted images having varying contrast levels, saturation levels, exposure levels and motion distractions.

BACKGROUND

Various medical device technologies are available to medical professionals for use in viewing and imaging internal organs and systems of the human body. For example, a medical endoscope equipped with a digital camera may be used by physicians in many fields of medicine in order to view parts of the human body internally for examination, diagnosis, and during treatment. For example, a physician may utilize a digital camera coupled to an endoscope to view the treatment of a kidney stone during a lithotripsy procedure.

However, during some portions of a medical procedure, the images captured by the camera may experience a variety of complex exposure sequences and different exposure conditions. For example, during a lithotripsy procedure, a physician may view a live video stream captured by a digital camera positioned adjacent to a laser fiber being used to pulverize a kidney stone. During the procedure, the physician's view of the kidney stone may become obscured due to laser flashing and/or fast-moving kidney stone particulates. Specifically, the live images captured by the camera may include over-exposed and/or under-exposed regions. Further, the portions of the images including over-exposed and/or under-exposed regions may lose details of highlight and shadow regions and may also exhibit other undesirable effects, such as halo effects. Therefore, it may be desirable to develop image processing algorithms which enhance the images collected by the camera, thereby improving the clarity and accuracy of the visual field observed by a physician during a medical procedure. Image processing algorithms which utilize image fusion to enhance multi-exposure images are disclosed.

BRIEF SUMMARY

This disclosure provides design, material, manufacturing method, and use alternatives for medical devices. An example method of combining multiple images includes obtaining a first input image formed from a first plurality of pixels, wherein a first pixel of the plurality of pixels includes a first characteristic having a first value. The method also includes obtaining a second input image formed from a second plurality of pixels, wherein a second pixel of the second plurality of pixels includes a second characteristic having a second value. The method also includes subtracting the first value from the second value to generate a motion metric and generating a weighted metric map of the second input image using the motion metric.

Alternatively or additionally to any of the embodiments above, further comprising converting the first input image to a first greyscale image, and converting the second input image to a second greyscale image.

Alternatively or additionally to any of the embodiments above, wherein the first characteristic is a first greyscale intensity valve, and wherein the second characteristic is a second greyscale intensity value.

Alternatively or additionally to any of the embodiments above, wherein the first input image is formed at a first time point, and wherein the second input image is formed at a second time point occurring after the first time point.

Alternatively or additionally to any of the embodiments above, wherein the first image and the second image have different exposures.

Alternatively or additionally to any of the embodiments above, wherein the first image and the second image are captured by a digital camera, and wherein the digital camera is positioned at the same location when it captures the first image and the second image.

Alternatively or additionally to any of the embodiments above, wherein the first plurality of pixels are arranged in a first coordinate grid, and wherein the first pixel is located at a first coordinate location of the first coordinate grid, and wherein second plurality of pixels are arranged in a second coordinate grid, and wherein the second pixel is located at a second coordinate location of the second coordinate grid, and wherein the first coordinate location is at the same respective location as the second coordinate location.

Alternatively or additionally to any of the embodiments above, wherein generating a motion metric further comprises weighing the motion metric using a power function.

Alternatively or additionally to any of the embodiments above, further comprising generating a contrast metric, a saturation metric and an exposure metric.

Alternatively or additionally to any of the embodiments above, further comprising multiplying the contrast metric, the saturation metric, the exposure metric and the motion metric together to generate the weighted metric map.

Alternatively or additionally to any of the embodiments above, further comprising using the weighted metric map to create a fused image from the first image and the second image.

Alternatively or additionally to any of the embodiments above, wherein using the weighted metric map to create a fused image from the first image and the second image further includes normalizing the weighted metric map.

Another method of combining multiple images includes using an image capture device of an endoscope to obtain a first image at a first time point and to obtain a second image at a second time point, wherein the image capture device is positioned at the same location when it captures the first image at the first time point and the second image at a second time point, and wherein the second time point occurs after the first time point. The method also includes converting the first input image to a first grey scale image, converting the second input image to a second greyscale image, generating a motion metric based on a characteristic of a pixel of both the first greyscale image and the second greyscale image, wherein the pixel of the first greyscale image has the same coordinate location of the pixel of the second greyscale image in their respective images. The method also includes generating a weighted metric map using the motion metric.

Alternatively or additionally to any of the embodiments above, wherein the characteristic of the pixel of the first image is a first grayscale intensity valve, and wherein the characteristic of the pixel of the second image is a second greyscale intensity value.

Alternatively or additionally to any of the embodiments above, wherein generating a motion metric further comprises weighing the motion metric using a power function.

Alternatively or additionally to any of the embodiments above, further comprising generating a contrast metric, a saturation metric and an exposure metric based on a characteristic of the pixel of the second image.

Alternatively or additionally to any of the embodiments above, further comprising multiplying the contrast metric, the saturation metric, the exposure metric and the motion metric together to generate the weighted metric map.

Alternatively or additionally to any of the embodiments above, further comprising normalizing the weighted metric map across the first image and the second image.

Alternatively or additionally to any of the embodiments above, further comprising using the normalized weighted metric map to create a fused image from the first image and the second image.

An example system for generating a fused imaged from multiple images obtained from an endoscope includes a processor operatively connected to the endoscope and a non-transitory computer-readable storage medium comprising code configured to perform a method of fusing images, the method comprising obtaining a first input image from the endoscope, the first input image formed from a first plurality of pixels, wherein a first pixel of the plurality of pixels includes a first characteristic having a first value. The method also includes obtaining a second input image from the endoscope, the second input image formed from a second plurality of pixels, wherein a second pixel of the second plurality of pixels includes a second characteristic having a second values. The method also includes subtracting the first value from the second value to generate a motion metric for the second pixel. The method also includes generating a weighted metric map using the motion metric.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
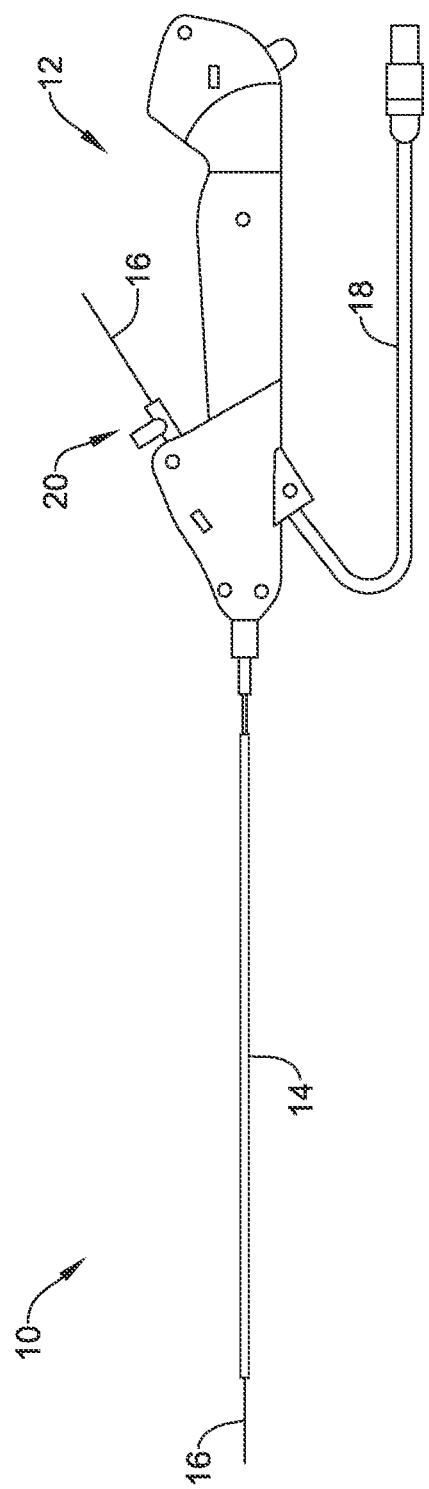
FIG. 1 is a schematic illustration of an example endoscopic system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Image processing methods performed on images collected via a medical device (e.g., an endoscope) during a medical procedure are described herein. Further, the image processing methods described herein may include an image fusion method. Various embodiments are disclosed for an improved image fusion method that preserves desirable portions of a given image (e.g., edges, texture, saturated colors, etc.) while minimizing undesirable portions of the image (e.g., artifacts from moving particles, laser flash, halo-effects, etc.). Specifically, various embodiments are directed to selecting the desirable portions of multi-exposure images and generating a weighted metric map for purposes of improving the overall resolution of a given image. For example, a fused image may be generated whereby over-exposed and/or under-exposed and/or blurred regions created by moving particles are represented with minimal degradation.

A description of a system for combining multi-exposure images to generate a resultant fused image is described below. FIG. 1 illustrates an example endoscopic system that may be used in conjunction with other aspects of the disclosure. In some embodiments, the endoscopic system may include an endoscope 10. The endoscope 10 may be specific to a particular endoscopic procedure, such as, e.g., ureteroscopy, lithotripsy, etc. or may be a general-purpose device suitable for a wide variety of procedures. In some embodiments, the endoscope 10 may include a handle 12 and an elongate shaft 14 extending distally therefrom, wherein the handle 12 includes a port configured to receive a laser fiber 16 extending within the elongate shaft 14. As illustrated in FIG. 1, the laser fiber 16 may be passed into a working channel of the elongate shaft 14 through a connector 20 (e.g., a Y-connector) or other port positioned along the distal region of the handle 12. It can be appreciated that the laser fiber 16 may deliver laser energy to a target site within the body. For example, during a lithotripsy procedure, the laser fiber 16 may deliver laser energy to pulverize a kidney stone.

Additionally, the endoscopic system shown in FIG. 1 may include a camera and/or lens positioned at the distal end of the elongate shaft 14. The elongate shaft and/or camera/lens may have deflection and/or articulation capabilities in one or more directions for viewing patient anatomy. In some embodiments, the endoscope 10 may be a ureteroscope. However, other medical devices, such as a different endoscope or related system, may be used in addition to or in place of a ureteroscope. Further, in some embodiments, the endoscope 10 may be configured to deliver fluid from a fluid management system to a treatment site via the elongate shaft 14. The elongate shaft 14 may include one or more working lumens for receiving a flow of fluid and/or other medical devices therethrough. In some embodiments, the endoscope 10 may be connected to the fluid management system via one or more supply lines.

In some embodiments, the handle 12 of the endoscope 10 may include a plurality of elements configured to facilitate the endoscopic procedure. In some embodiments, a cable 18 may extend from the handle 12 and is configured for attachment to an electronic device (not pictured) such as e.g. a computer system, a console, a microcontroller, etc. for providing power, analyzing endoscopic data, controlling the endoscopic intervention, or performing other functions. In some embodiments, the electronic device to which the cable 18 is connected may have functionality for recognizing and exchanging data with other endoscopic accessories.

In some embodiments, image signals may be transmitted from the camera at the distal end of the endoscope through the cable 18 to be displayed on a monitor. For example, as described above, the endoscopic system shown in FIG. 1 may include at least one camera to provide a visual feed to the user on the display screen of a computer workstation. It can be appreciated that, while not explicitly shown, the elongate shaft 14 may include one or more working lumens within which a data transmission cable (e.g., fiber optic cable, optic cable, connector, wire, etc.) may extend. The data transmission cable may be connected to the camera described above. Further, the data transmission cable may be coupled to the cable 18. Further yet, the cable 18 may be coupled to the computer processing system and display screen. Images collected by the camera may be transmitted through a data transmission cable positioned within the elongate shaft 14, whereby the image data then passes through the cable 18 to the computer processing workstation.

In some embodiments, the workstation may include a touch panel computer, an interface box for receiving the wired connection (e.g., the cable 18), a cart, and a power supply, among other features. In some embodiments, the interface box may be configured with a wired or wireless communication connection with the controller of the fluid management system. The touch panel computer may include at least a display screen and an image processor, and in some embodiments, may include and/or define a user interface. In some embodiments, the workstation may be a multi-use component (e.g., used for more than one procedure) while the endoscope 10 may be a single use device, although this is not required. In some embodiments, the workstation may be omitted and the endoscope 10 may be electronically coupled directly to the controller of the fluid management system.

Figure 2:
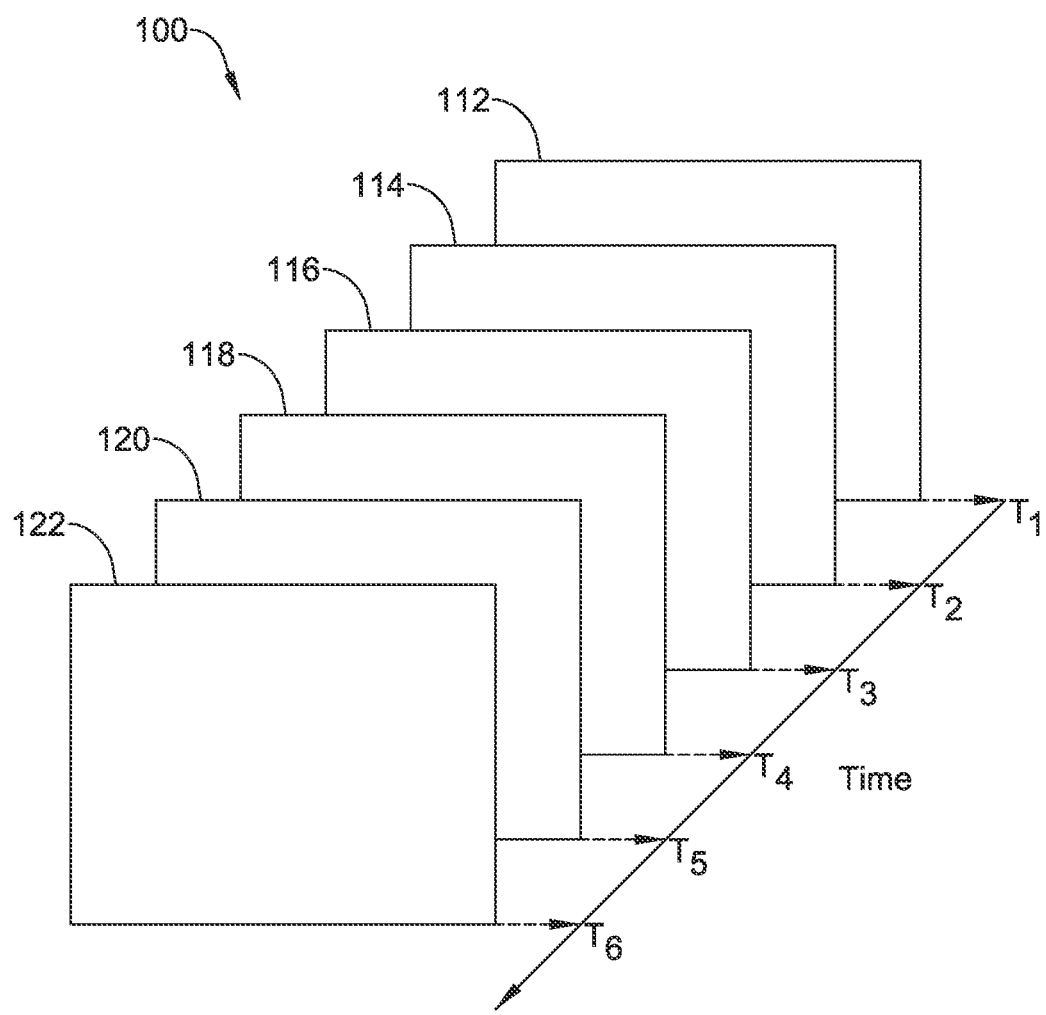
FIG. 2 illustrates a sequence of images collected by digital camera over a time period.

FIG. 2 illustrates a plurality of images 100 captured in sequence by a camera over a time period. It can be appreciated that the images 100 may represent a sequence of images captured during a medical procedure. For example, the images 100 may represent a sequence of images captured during a lithotripsy procedure in which a physician utilizes a laser fiber to treat a kidney stone. It can be further appreciated that the images 100 may be collected by an image processing system which may include, for example, a computer workstation, laptop, a tablet, or other computing platform that includes a display through which a physician may visualize the procedure in real-time. During the real-time collection of images 100, the image processing system may be designed to process and/or enhance a given image based on the fusion of one or multiple images taken subsequent to a given image. The enhanced images may then be visualized by the physician during the procedure.

As discussed above, it can be appreciated that the images 100 illustrated in FIG. 2 may include images captured with an endoscopic device (i.e. an endoscope) during a medical procedure (e.g., during a lithotripsy procedure). Further, it can be appreciated that the images 100 illustrated in FIG. 2 may represent a sequence of images 100 captured over time. For example, the image 112 may represent an image captured at time point $T_1$, while the image 114 may represent an image captured at time point $T_2$, whereby the image 114 captured at time point $T_2$ occurs after the image 112 captured at time point $T_1$. Further, the image 116 may represent an image captured at time point $T_3$, whereby the image 116 captured time point $T_3$ occurs after the image 114 captured at time point $T_2$. This sequence may progress for the images 118, 120 and 122 taken at time points $T_4$, $T_5$ and $T_6$, respectively, where time point $T_4$ occurs after time point $T_5$, time point $T_5$ occurs after time point $T_4$, and time point $T_6$ occurs after time point $T_5$.

It can further be appreciated that the images 100 may be captured by a camera of an endoscopic device having a fixed position during a live event. For example, the images 100 may be captured by a digital camera having a fixed position during a medical procedure. Therefore, it can further be appreciated that while the camera's field of view remains constant during the procedure, the images that are generated during the procedure may change due to the dynamic nature of the procedure being captured by the images. As a simple example, the image 112 may represent an image taken at a time point just before a laser fiber emits laser energy to pulverize a kidney stone. Further, the image 114 may represent an image taken at a time point just after a laser fiber emits laser energy to pulverize the kidney stone. Because the laser emits a bright flash of light, it can be appreciated that the image 112 captured just prior to the laser emitting the light may be very different in terms of saturation, contrast, exposure, etc. as compared to the image 114. In particular, the image 114 may include undesirable characteristics compared to the image 112 due to the sudden release of laser light. Additionally, it can further be appreciated that after the laser imparts energy to the kidney, various particles from the kidney may move quickly through the camera's field of view. These fast-moving particles may manifest as localized regions of undesirable image features (e.g., over-exposure, under-exposure, etc.) through a series of images over time.

It can be appreciated that a digital image (such as any one of the plurality of images 100 shown in FIG. 1) may be represented as a collection of pixels (or individual picture elements) arranged in a 2-dimensional grid, represented using squares. Further, each individual pixel making up an image may be defined as the smallest item of information in the image. Each pixel is a small sample of the original image, where more samples typically provide more-accurate representations of the original.

Figure 3:
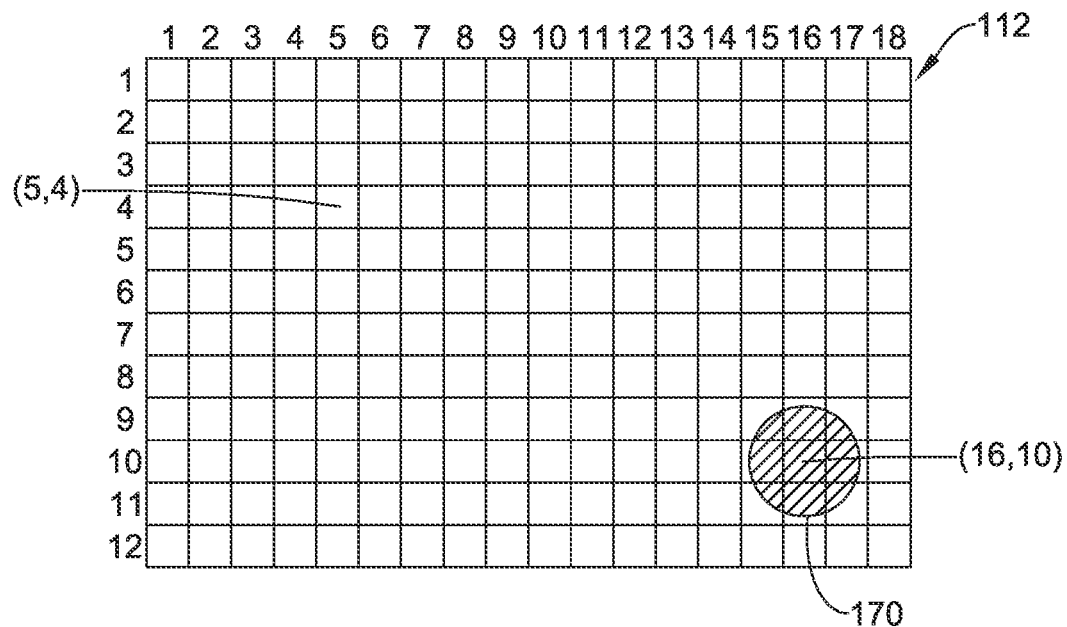
FIG. 3 illustrates a first image and a second image of the collection of images illustrated in FIG. 2.
Figure 3:
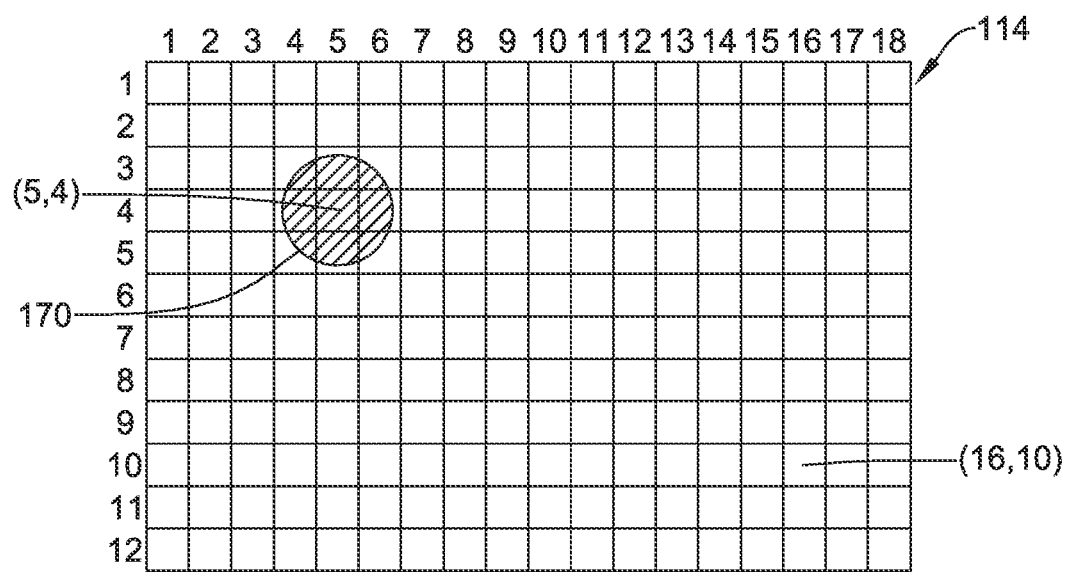

For example, FIG. 3 shows the example digital image 112 and the digital image 114 of FIG. 2 represented as a collection of pixels arranged in a 2-dimensional grid. For simplicity, the grid for each of the image 112 and the image 114 is sized to 18×12. In other words, the 2-dimensional grid for images 112/114 includes 18 columns of pixels extending vertically and 12 rows of pixels extending horizontally. It can be appreciated that the size of the images represented in FIG. 3 is exemplary. The size (total number of pixels) for digital images may vary. For example, a common size for digital images may include images have 1080-pixel columns by 720-pixel rows (e.g., a frame dimension of 1080×720).

It can be appreciated that an individual pixel location may be identified via its coordinates (X,Y) on the 2-dimensional image grid. Additionally, comparison of adjacent pixels within a given image may yield desirable information about what portions of a given image an algorithm may seek to preserve when performing image enhancement (e.g., image fusion). For example, FIG. 3 illustrates an image feature 170 generally centered at a pixel location (16, 10) in the lower right corner of the image. It can be appreciated that the pixels making up the feature 170 are substantially darker as compared to the pixels surrounding the feature 170. Therefore, these the pixels representing the feature 170 may have a high contrast value compared to the pixels surrounding the feature 170. This high contrast may be an example of valuable information of the image. Other valuable information may include high saturation, edges, and texture.

Additionally, it can be further appreciated that the information represented by a pixel at a given coordinate may be compared across multiple images. Comparison of identical-coordinate pixels across multiple images may yield desirable information about portions of a given image that an image processing algorithm may seek to discard when performing image enhancement (e.g., image fusion).

For example, the image 114 in FIG. 3 illustrates that the feature 170 may represent a moving particle being captured by two images over time. Specifically, FIG. 3 illustrates that the feature 170 (shown in the lower right corner of image 112) has moved to the upper left corner of the image 114. It is noted that images 112/114 are captured with the same image capture device (e.g., digital camera) from the same image capture location and map, pixel-per-pixel, with one another. Pixel-based subtraction of the two images may generate a new image with all pixel values close to zero other than the location (16,10) and the location (5, 4), which may provide information that can be utilized by an algorithm of an image processing system to reduce the undesirable effects of the moving particle. For example, the image processing system may create a fused image of image 112 and image 114, whereby the fused image retains the desirable information of each image while discarding the undesirable information.

The basic mechanism of generating a fused image may be described as pixels in the input images having different exposures and are weighted according to different "metrics" such as contrast, saturation, exposure and motion. These metric weightings can be used to determine how much a given pixel in an image being fused with one or more images will contribute to the final fused image.

A method by which a plurality of differently exposed images (1 ... N) of an event (e.g., a medical procedure) may be fused by an image processing algorithm into a single fused image is disclosed in FIGS. 4-5. For simplicity, the image processing algorithm illustrated in FIGS. 4-5 will be described using a raw image 114 and its "previous" image 112 (both shown in FIGS. 2-3) as an example. However, it can be appreciated that an image processing algorithm may utilize any number of images captured during an event to generate one or more fused images.

It should be appreciated that the fusion process may be performed by an image processing system and output to a display device, whereby the final fused image maintains the desirable features of the image metrics (contrast, saturation, exposure, motion) from input images 1 through N.

Figure 4:
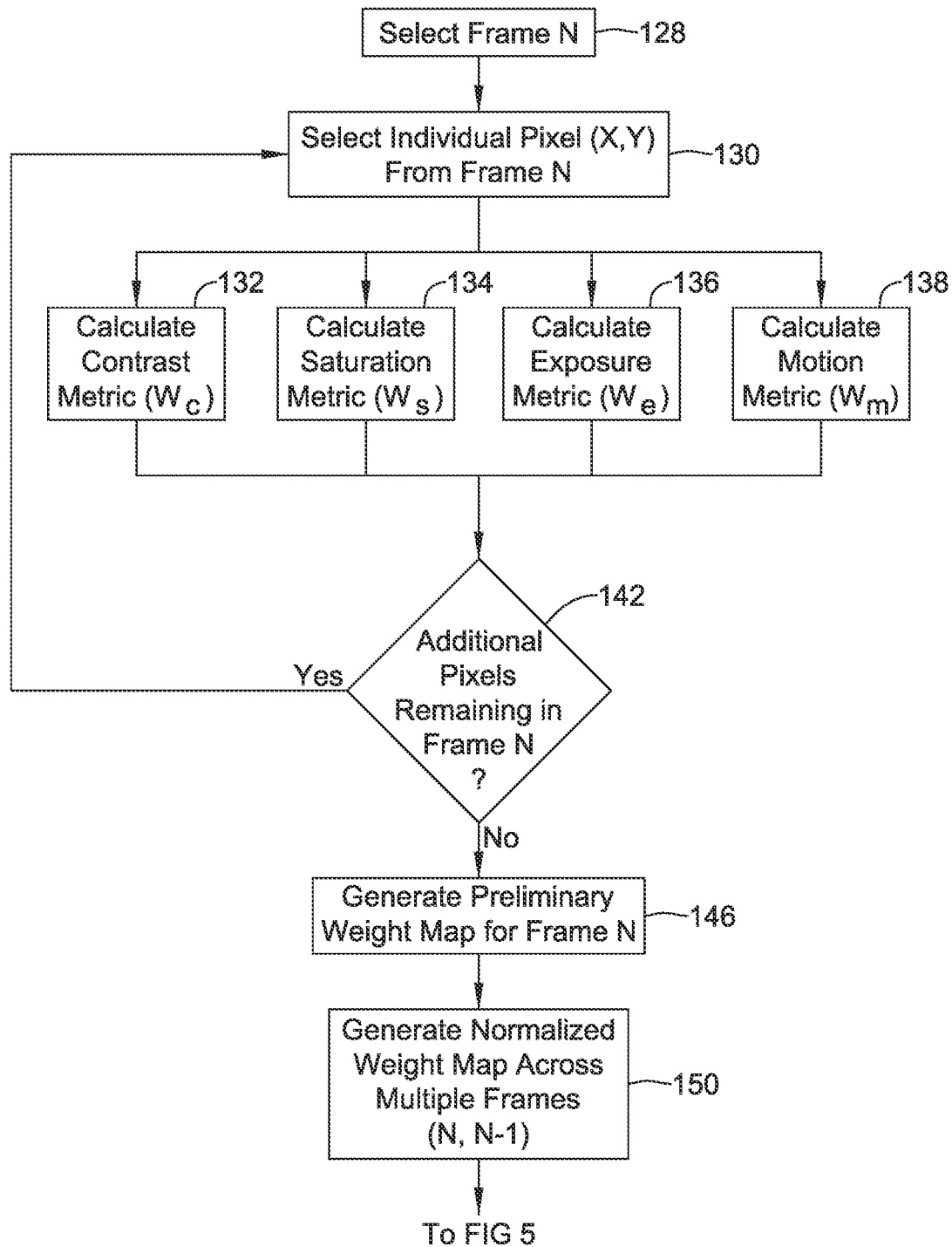
FIGS. 4-5 is a block diagram of an image processing algorithm for using a weighted image map to generate a fused image from multiple raw images.
Figure 5:
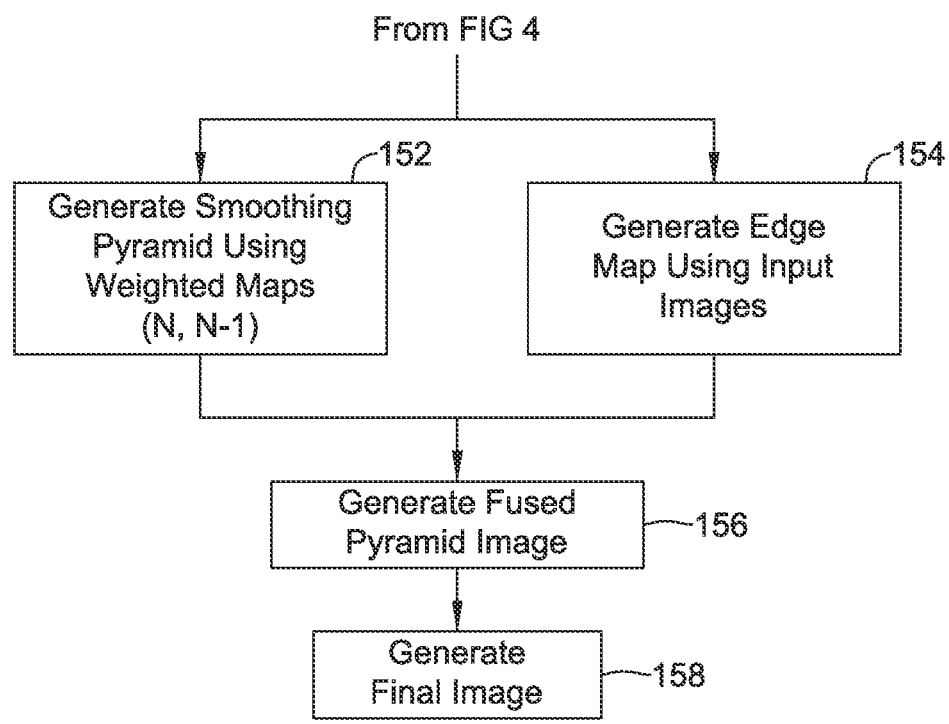

FIGS. 4-5 illustrate an example step to generate an example weight map for a fused image. An example first step may include selecting 128 an initial input image. For the discussion herein, the example input image 114 will be described as an initial input image which will be fused with its previous image 112 (referring to the above discussion, it is noted that the image 114 was captured after the image 112).

After selecting the input image 114, an individual contrast metric, saturation metric, exposure metric and motion metric will be calculated at each of the individual pixel coordinates making up the image 114. In the exemplary embodiment, there are 216 individual pixel coordinates making up the image 114 (referring back to FIG. 3, the example image 114 includes 216 individual pixels in the 18×12 grid). As will be described in greater detail below, each of the contrast metric, saturation metric, exposure metric and motion metric will be multiplied together at each pixel location (i.e., pixel coordinate) for the image 114, thereby generating a "preliminary weight map" for imagine 114 (for reference, this multiplication step is described by text box 146 in FIG. 4). However, prior to generating the preliminary weight map for an image, each individual contrast metric, saturation metric, exposure metric and motion metric needs to be calculated for each pixel location. The following discussion describes the calculation of the contrast metric, saturation metric, exposure metric and motion metric for each pixel location.

Calculation of Contrast Metric

Calculation of the contrast metric is represented by text box 132 in FIG. 4. To calculate the contrast metric for each pixel location, a Laplacian filter may be applied to the image to create a greyscale version of the image. After the greyscale version of the image is created, the absolute value of the filter response may be taken. It is noted that the contrast metric may assign a high weight to important elements such as edges and texture of an image. The contrast metric (calculated for each pixel) may be represented herein as ($W_e$).

Calculation of Saturation Metric

Calculation of the saturation metric is represented by text box 134 in FIG. 4. To calculate the saturation metric for each pixel location, the standard deviation within the R, G and B channel is taken (at each given pixel). A lower standard deviation means that the R, G and B values are close together (e.g., the pixel is more of a grey color). It can be appreciated that a grey pixel may not contain as much valuable information as other colors, such as red (because, for example, the human anatomy includes more reddish colors). However, if a pixel has a higher standard deviation, the pixel tends to be more reddish, greenish or blueish, which contains more valuable information. It is noted that saturated colors are desirable and make an image look vivid. The saturation metric (calculated for each pixel) may be represented herein as ($W_s$).

Calculation of Exposure Metric

Calculation of the exposure metric is represented by text box 136 in FIG. 4. The raw light intensity for a given pixel channel may provide an indication of how well a pixel is exposed. It is noted that each individual pixel may include three separate channels for red, green and blue colors (RGB), all of which may be displayed at a certain "intensity." In other words, the overall intensity of a pixel location (i.e., coordinate) may be the sum of a red channel (at a certain intensity), a green channel (at a certain intensity) and a blue channel (at a certain intensity). These RGB light intensities at a pixel location may fall within a range of 0-1, whereby values near zero are under-exposed and values near 1 are over-exposed. It is desirable to keep intensities that are not at the ends of the spectrum (not near 0 or near 1). Hence, to calculate the exposure metric for a given pixel, each channel is weighted based on how close it is to the median of a reasonably symmetric unimodal distribution. For example, each channel may be weighted based on how close it is to a given value on a Gaussian curve, or any other type of distribution. After determining the weightings for each RGB color channel at an individual pixel location, the three weightings are multiplied together to arrive at the overall exposure metric for that pixel. The exposure metric (calculated for each pixel) may be represented herein as ($W_e$).

Calculation of Motion Metric

Figure 6:
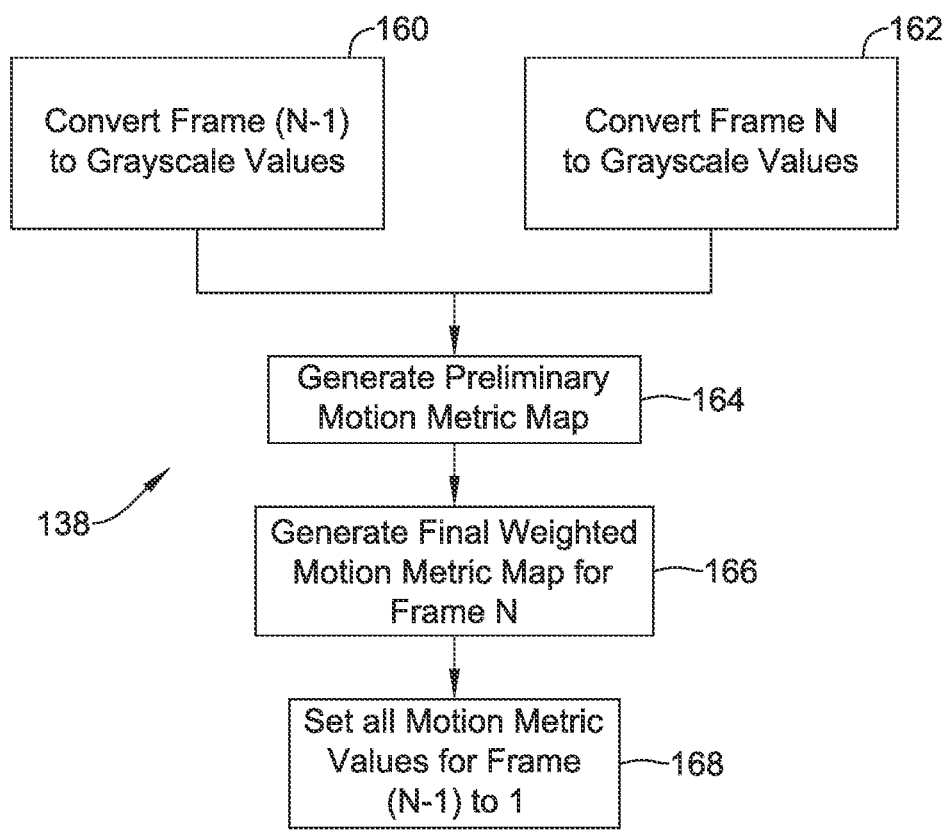
FIG. 6 is a block diagram of an image processing algorithm for generating a weighted motion metric map for an image.

Calculation of the motion metric is represented by text box 138 in FIG. 4. A more detailed discussion regarding calculation of the motion metric is set forth in the block diagram shown at FIG. 6. The motion metric is designed to suppress the distractions caused by flying particles, laser flash, or dynamic, fast-changing scenes occurring across multiple frames. The motion metric for a given pixel location is calculated using an input image (e.g., 114) and its previous image (e.g., image 112). An example first step in calculating the motion metric for each pixel location of image 114 is to convert 160 all the colored pixels in the image 114 to a greyscale value. For example, it can be appreciated that, in some instances, the raw data for each pixel location in the image 114 may be represented as integer data whereby each pixel location may be converted to a greyscale value between 0-255. However, in other examples, the raw integer values may be converted to other data types. For example, the greyscale integer values of the pixels may be converted to float type, whereby each pixel may be assigned a greyscale value from 0-1 and then divided by 255. In these examples, a completely black pixel may be assigned a value of 0 and a completely white pixel is assigned a value of 1. Further, while the above examples discuss representing the raw image data as integer data or float type, it can be appreciated that the raw image data may be represented by any data type.

After converting the example frame 114 to greyscale values, an example second step in calculating the motion metric for each pixel location of image 114 is to convert 162 all the colored pixels in the frame 112 to a greyscale value using the same methodology as described above.

After converting each pixel location of the frame 114 and the frame 112 to greyscale, the example third step 164 in calculating the motion metric for each pixel location of image 114 is to subtract the greyscale value of each pixel location of image 112 from the greyscale value of the corresponding pixel location of the image 114. For example, if the greyscale value of the pixel coordinate (16,10) of image 114 (shown in FIG. 3) equals 0.90, and the corresponding greyscale pixel coordinate (16,10) of image 112 (shown in FIG. 3) equals 0.10, the motion subtraction value for the pixel (16,10) of image 114 equals 0.80 (0.90 minus 0.10). This subtracted motion value (e.g., 0.80) will be stored as a representative motion metric value for the pixel (16,10) in image 114. As discussed above, the motion metric value will be used to generate a fused image based on algorithms discussed below Further, it can be appreciated that the subtraction value may be negative, which may indicate that the artifact is in the image 112. The negative values will be set to zero for the ease of the weighting factor calculation.

It can be appreciated that for fast moving objects, the subtracted motion values for a given pixel coordinate may be large because the change in the pixel grayscale value will be dramatic (e.g., as a fast-moving object is captured moving through multiple images, the grayscale colors of the individual pixels defining the object will change dramatically from image to image). Conversely, for slow moving objects, the motion values for a given pixel coordinate may be small because the change in pixel grayscale values will be more gradual (e.g., as a slow-moving object is captured moving through multiple images, the grayscale colors of the individual pixels defining the object will change slowly from image to image).

After the subtracted motion values have been calculated for each pixel location in the most recent image (e.g., image 114), an example fourth step 166 in calculating the motion metric for each pixel location of image 114 is to weigh each subtracted motion value for each pixel location based on how close it is to zero. One weight calculation, using a power function, is set forth in Equation 1 below:

$$W_m = (1-[\text{subtracted motion value}])^{\wedge}100 \qquad (1)$$

Other weight calculations are also possible and not limited to the power function noted above. Any function that makes the weight close to 1 with zero motion value and quickly goes to 0 with increasing motion value is possible. For example, one could use the following weight calculation set for in Equation 2 below:

$$W_m = \begin{cases} 1 - 10*[\text{motion value}]; & \text{motion value} < 0.1 \\ 0; & \text{motion value} \geq 0.1 \end{cases} \qquad (2)$$

These values are the weighted motion metric values for each pixel in the image 114 and may be represented in as ($W_m$).

It can be appreciated that for pixels representing still objects, the subtracted motion values will be closer to zero, so the $W_m$ will be close to 1. Conversely, for moving objects, the subtracted motion value will be closer to 1, so the $W_m$ will be close to 0. Returning to our example of the fast-moving dark circle 170 moving through the images 114/112, the pixel (16,10) rapidly changes from a darker color in image 112 (e.g., greyscale value of 0.90) to a lighter color in image 114 (e.g., greyscale value of 0.10). The resultant subtracted motion value equals 0.80 (closer to 1) and the weighted motion metric for pixel location (16,10) of image 114 will be: $(1-0.80)^{\wedge}100$, or very close to 0.

It should be noted that the $W_m$ for previous images (e.g., the image 112), will be set to 1. In this way, for the area of still objects, the $W_m$ for both image 112 and image 114 are close to 1, so they have the same weight regarding the motion metric. The final weight map of the still object will depend on the contrast, exposure and saturation metrics. For the area of moving objects or laser flash, the $W_m$ for image 112 will still be 1 and the $W_m$ for image 114 will be close to 0, so the final weight of these areas in image 114 will be much smaller than that in image 112. Small weight value will discard pixels of the frame into the fused frame, while larger weight value will bring the pixel of the frame into the fused image. In this way, the artifacts will be removed from the final fused image.

FIG. 4 further illustrates that after the contrast metric ($W_c$), the saturation metric ($W_s$), the exposure metric ($W_e$) and the motion metric ($W_m$) have been calculated for each pixel of the image 114, a preliminary weight map may be generated 146 for the image 114 by multiplying all four metric values (of a given pixel) together at each individual pixel location for the image 114 (the calculation is set forth in Equation 3 below). As represented in FIG. 4, Equation 3 would be performed at each individual pixel location (e.g., (1,1), (1,2), (1,3) . . . and so forth) for all 216 example pixels in image 114 to generate the preliminary weight map.

$$W=(W_c)*(W_s)*(W_e)*(W_m) \quad (3)$$

FIG. 4 illustrates that after the preliminary weight map for an example image (e.g., image 114) has been generated, an example next step may include normalizing 150 the weight maps across multiple images. The purpose of this step may be to make the sum of the weighted values for each pixel location (in any two images being fused) to equal 1. The equation for normalizing a pixel location (X,Y) for an example "Image 1" and example "Image 2" (for which preliminary weight maps have already been generated using the above methodology) is shown in Equation 4 and Equation 5 below:

$$W_{Image1}(X,Y)=W_{Image1}(X,Y)/(W_{Image1}(X,Y)W_{Image2}(X,Y)) \quad (4)$$

$$W_{Image2}(X,Y)=W_{Image2}(X,Y)/(W_{Image1}(X,Y)W_{Image2}(X,Y)) \quad (5)$$

As an example, assume two images, Image 1 and Image 2, each have a preliminary weight map having pixel location (14,4), whereby the preliminary weighted value for the pixel (14,4) of Image 1=0.05 and the preliminary weighted value for the pixel (14,4) of Image 2=0.15. The normalized values for pixel location (14,4) for Image 1 are shown in Equation 6 and the normalized values for pixel location (14,4) for Image 2 are shown in Equation 7 below:

$$W_{Image1}(14,4)=0.05/(0.05+0.15)=0.25 \quad (6)$$

$$W_{Image2}(14,4)=0.15/(0.05+0.15)=0.75 \quad (7)$$

As discussed above, it is noted that the sum of the normalized weighted values of Image 1 and Image 2 at the pixel location (14,4) equals 1.

FIG. 5 illustrates an example next step in generating a fused image from two or more example images (e.g., images 112/114) (it is noted that at this point in the algorithm shown in FIGS. 4-5 and described above, each example image 112/114 may have an original input image and a normalized weighted map). The example step may include generating 152 a smoothing pyramid from the normalized weight map (for each image). The smoothing pyramid may be calculated as follows:

G1=W
G2=downsample(G1, filter)
G3=downsample(G2, filter)

The above calculation continues until the Gx size is less than the size of the smoothing filter, which is a lowpass filter (e.g., a Gaussian filter).

FIG. 5 illustrates that the example step may further include generating 154 an edge map from the input images (for each image). The edge map contains the texture information of the input image at different scales. For example, assume the input image is denoted as "I." The edge map at level x can be denoted as Lx and is calculated in the following steps:

I1=downsample(I, filter)
L1=I−upsample(I1)
I2=downsample(I1, filter)
L2=I1−upsample(I2)
I3=downsample(I2, filter)
L3=I2−upsample(I3)

This calculation continues until the Ix size is less than the size of the edge filter, which is a high pass filter (e.g., a Laplacian filter).

FIG. 5 illustrates another example next step in generating a fused image from two or more example images (e.g., images 112/114). For example, for each input image, the edge map (described above) may be multiplied with the smoothing map (described above). The resultant maps generated by multiplying the edge map with the smoothing map for image, may be added together to form a fused pyramid. This step is represented by the text box 156 in FIG. 5.

FIG. 5 illustrates a final example in generating a fused image, as represented by text box 158 in FIG. 5. This step includes performing the following calculations on the fused pyramid:

IN=LN
RN=upsample(IN, filter)
IN−1=LN−1+RN
RN−1=upsample(IN−1, filter)
IN−2=LN−2+RN−1
RN−2=upsample(IN−2, filter)
IN−3=LN−3+RN−2

The calculation continues until we reach the L1 level, where the calculated I1 is the final image.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of combining multiple images obtained from an endoscope, the method comprising:
    obtaining a first input image formed from a first plurality of pixels arranged in a first coordinate grid, wherein each pixel of the plurality of pixels is located at a coordinate location of the first coordinate grid;
    obtaining a second input image formed from a second plurality of pixels arranged in a second coordinate grid, wherein each pixel of the second plurality of pixels is located at a coordinate location of the second coordinate grid, and wherein the coordinate locations of the first plurality of pixels of the first coordinate grid are at the same respective locations as the coordinate locations of the plurality of pixels of the second coordinate grid;

converting each pixel of the first plurality of pixels of the first input image to a grayscale intensity value to a create a first grayscale image;

converting each pixel of the second plurality of pixels of the second input image to a grayscale intensity value to create a second grayscale image;

subtracting the grayscale intensity value for each pixel coordinate location of the first plurality of pixels from the grayscale intensity value for each pixel coordinate location of the second plurality of pixels to generate a motion metric for each pixel coordinate location in the second coordinate grid;

generating a weighted metric map of the second input image using the motion metric for each pixel coordinate location in the second coordinate grid, wherein the weight metric map is configured to determine the amount each pixel in the first plurality of pixels and each pixel in the second plurality of pixels will contribute to a fused image of the first input image and the second input image in order to remove artifacts present in one of the first input image and the second input image from the fused image.

2. The method of claim 1, wherein the first input image is formed at a first time point, and wherein the second input image is formed at a second time point occurring after the first time point.

3. The method of claim 1, wherein the first image and the second image have different exposures.

4. The method of claim 3, wherein the first image and the second image are captured by a digital camera of the endoscope, and wherein the digital camera is positioned at the same location when it captures the first image and the second image.

5. The method of claim 1, wherein generating a motion metric further comprises weighing the motion metric using a power function.

6. The method of claim 1, further comprising generating a contrast metric, a saturation metric and an exposure metric.

7. The method of claim 6, further comprising multiplying the contrast metric, the saturation metric, the exposure metric and the motion metric together to generate the weighted metric map.

8. The method of claim 1, wherein using the weighted metric map to create a fused image from the first image and the second image further includes normalizing the weighted metric map.

9. A method of combining multiple images during an endoscopic procedure, the method comprising:

using an image capture device of an endoscope to obtain a first image at a first time point and to obtain a second image at a second time point, wherein the image capture device is positioned at the same location when it captures the first image at the first time point and the second image at a second time point, and wherein the second time point occurs after the first time point;

converting the first input image to a first grayscale image;

converting the second input image to a second grayscale image;

generating a motion metric based on a characteristic of a pixel of both the first grayscale image and the second grayscale image, wherein the pixel of the first grayscale image has the same coordinate location of the pixel of the second grayscale image in their respective images; and generating a weighted metric map using the motion metric.

10. The method of claim 9, wherein the characteristic of the pixel of the first image is a first grayscale intensity valve, and wherein the characteristic of the pixel of the second image is a second grayscale intensity value.

11. The method of claim 9, wherein generating a motion metric further comprises weighing the motion metric using a power function.

12. The method of claim 11, further comprising generating a contrast metric, a saturation metric and an exposure metric based on a characteristic of the pixel of the second image.

13. The method of claim 12, further comprising multiplying the contrast metric, the saturation metric, the exposure metric and the motion metric together to generate the weighted metric map.

14. The method of claim 13, further comprising normalizing the weighted metric map across the first image and the second image.

15. The method of claim 14, further comprising using the normalized weighted metric map to create a fused image from the first image and the second image.

16. A system for generating a fused image from a first input image and a second input image obtained from an endoscope, comprising:

a processor operatively connected to the endoscope; and a non-transitory computer-readable storage medium comprising code configured to perform a method of generating a fused image based on the first input image and the second input image, the method comprising:

obtaining the first input image from the endoscope, the first input image formed from a first plurality of pixels, wherein a first pixel of the plurality of pixels includes a first characteristic having a first value;

obtaining the second input image from the endoscope, the second input image formed from a second plurality of pixels, wherein a second pixel of the second plurality of pixels includes a second characteristic having a second value;

subtracting the first value from the second value to generate a motion metric for the second pixel; and generating a weighted metric map using the motion metric, wherein the weighted metric map is configured to determine the amount the second pixel will contribute to the fused image of the first input image and the second input image in order to remove artifacts present in one of the first input image and the second input image from the fused image.

* * * * *